Figure 1:
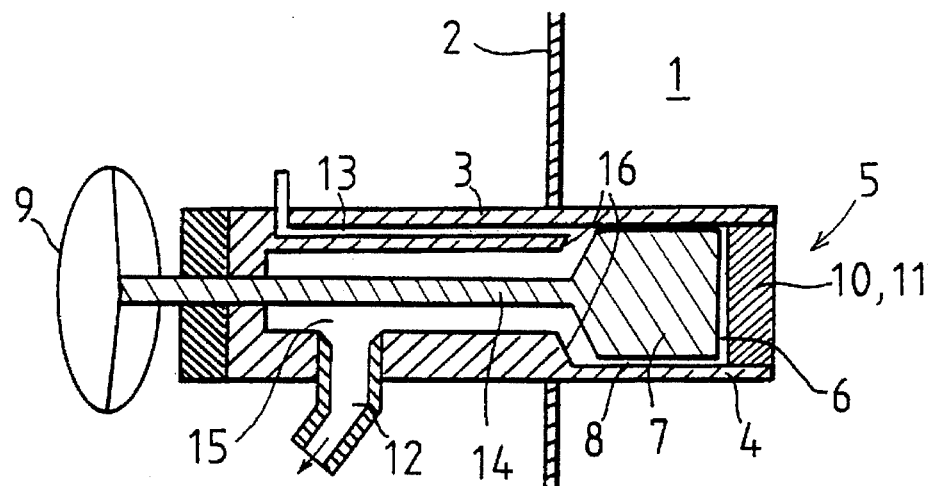

United States Patent [19]

Piirainen et al.

[11] Patent Number: 5,625,157
[45] Date of Patent: Apr. 29, 1997

[54] DEVICE FOR TAKING A FILTRATE SAMPLE FROM SLUSH PULP

[75] Inventors: Esa Piirainen; Teuvo Peltomäki, both of Kajaani, Finland

[73] Assignee: Kajaani Elektroniikka Oy, Kajaani, Finland

[21] Appl. No.: 574,411

[22] Filed: Dec. 15, 1995

[51] Int. Cl.$^6$ ........................................... G01N 1/22
[52] U.S. Cl. ........................................... 73/863.86
[58] Field of Search ............ 73/863.41, 863.51–863.57, 73/863.21, 863.23, 863.24, 863.81, 863.86; 251/324, 319

[56] References Cited

U.S. PATENT DOCUMENTS

| 4,053,354 | 10/1977 | Kitsnik . | |
|---|---|---|---|
| 4,458,543 | 7/1984 | Mieth | 73/863.86 |
| 4,594,904 | 6/1986 | Richter | 73/863.86 |

FOREIGN PATENT DOCUMENTS

| 46193 | 1/1973 | Finland . | |
|---|---|---|---|
| 57664 | 9/1980 | Finland . | |
| 694394 | 7/1953 | United Kingdom | 251/319 |

Primary Examiner—Robert Raevis
Attorney, Agent, or Firm—Beveridge, DeGrandi, Weilacher & Young, LLP

[57] ABSTRACT

Device for taking a filtrate sample from fibrous slush pulp through the wall (2) of a container (1) containing pulp, said device comprising a cylinder (3) mounted on the wall (2) so that it goes through the wall, with its open end (5) towards the container (1); a piston (7) placed in the cylinder space and forming a sampling duct (8) from the open cylinder end into the cylinder space behind the piston; and an actuator (9) for moving the piston into an intermediate position, in which the piston end forms a pocket (10) limited by the cylinder walls (4) and the piston end for gathering fibrous slush pulp and forming a pillow-like filter (11) in the pocket, and into a front position for removing the pillow-like filter into the container; the cylinder is provided with a drain duct (12) for draining off the sample penetrating through the filter and the sampling duct into the space behind the piston for analysis.

10 Claims, 1 Drawing Sheet

DEVICE FOR TAKING A FILTRATE SAMPLE FROM SLUSH PULP

The present invention relates to a device for taking a filtrate sample from slush pulp containing fibres through the wall of a pulp container.

In paper and cellulose industry and pulp industry in general, samples are taken from slush pulp to monitor and control the process. The slush pulp samples are analyzed to determine parameters relating to the fibres as well as parameters relating to the liquid contained in the pulp, i.e. to the filtrate, for instance pH. The present application is only concerned with the taking of a filtrate sample in general and with a device for taking a filtrate sample; the application is not at all concerned with the analysis of a filtrate sample, this can be done by any method known in itself from literature. In the present application, 'slush pulp' refers to any pulp containing fibres and water as used in paper, cellulose or wood fibre industry or clothing industry or in general in any industry involving processing of fibres in general, e.g. natural vegetable or animal fibres or synthetic fibres.

At present, it is common practice to take samples from desired stages of a given process by using sampling pipes, possibly provided with screens, or similar sampling devices. However, the pipes and screens used tend to get clogged by lignocellulose fibres contained in slush pulp. Known devices for the cleaning and washing of sampling equipment do not meet the requirements imposed on them, and current sampling devices are unsatisfactory especially when used for on-line monitoring of processes.

The object of the present invention is to eliminate the drawbacks described above. A specific object of the invention is to produce a new type of device for taking a filtrate sample from slush pulp containing fibres through the wall of a pulp container in a manner allowing the container to be cleaned under manual or automatic control when desired. A further object of the invention is to produce a device of this type that is more applicable for on-line monitoring of pulp filtrate samples in any pulp industry involving fibre processing than previously known devices and is more reliable than these.

As for the features characterizing the invention, reference is made to the claims.

The invention is based on a new design for a device for taking a filtrate sample. The device comprises a special cylinder space limited by walls. One end of the cylinder is partly or completely open, and the cylinder can be mounted in a container containing slush pulp so that the open end of the cylinder space opens into the container. Furthermore, the cylinder is provided with a piston-like reciprocating valve so mounted that it can move to and fro within the cylinder space and forms a sampling duct from the open cylinder end into the space behind the reciprocating valve. In addition, the device comprises an actuator for moving the reciprocating valve from an intermediate position into a front position. In the intermediate position, the reciprocating valve end has sunk through some distance into the open cylinder end, forming a special pocket at the cylinder end. Thus, the pocket is limited by the cylinder walls and the reciprocating valve end. The cylinder opens into the slush pulp container, so slush pulp is gathered in the pocket, forming in it a pillow-like fibre accumulation, a filter. In the front position, the piston end has been pushed at least mainly to the level of the open cylinder end to discharge the fibre accumulation into the container. Moreover, the cylinder is provided with a drain duct to drain off the filtrate sample which has penetrated through the fibre material gathered in the pocket and through the sampling duct into the space behind the reciprocating valve for analysis.

In a preferred embodiment, the reciprocating valve has a rear position in which the reciprocating valve is designed to close the drain duct. In this case, the reciprocating valve surface on the side facing towards the cylinder space behind the reciprocating valve may form e.g. a shutter which, when the reciprocating valve is in the rear position, covers the drain duct and closes it. Alternatively, the reciprocating valve or the piston rod moving the piston in its direction of motion may also be provided with a separate shutter element designed to close the drain duct in the rear position of the reciprocating valve and to open it in the front position of the reciprocating valve. It is naturally possible to use a separate closing valve in the drain duct.

In a preferred embodiment, the cylinder and reciprocating valve have a gap between them that forms a sampling duct. Alternatively, the reciprocating valve and/or the cylinder wall can be provided with a separate canal to form a sampling duct leading from the front side of the piston to its rear side.

Furthermore, the cylinder is preferably provided with a flushing duct to supply wash water into the sampling duct and/or drain duct to enable these to be washed. In this case, the reciprocating valve is preferably so designed that, when in the rear position, it closes the flushing duct as well so that no flush water can flow into the slush pulp container.

The invention allows a sample to be taken from the slush pulp in the container when the piston is in its intermediate position. The sample is passed through the liquid canal into the drain duct and further into an analyzer. After the sampling, the device can be cleansed and flushed with wash water. The cleansing of the device can be performed very easily and without effort, e.g. under automatic control. The device is easy to use and reliable in operation. The device is particularly applicable for taking filtrate samples from slush pulp in any process conditions.

Figure 2:
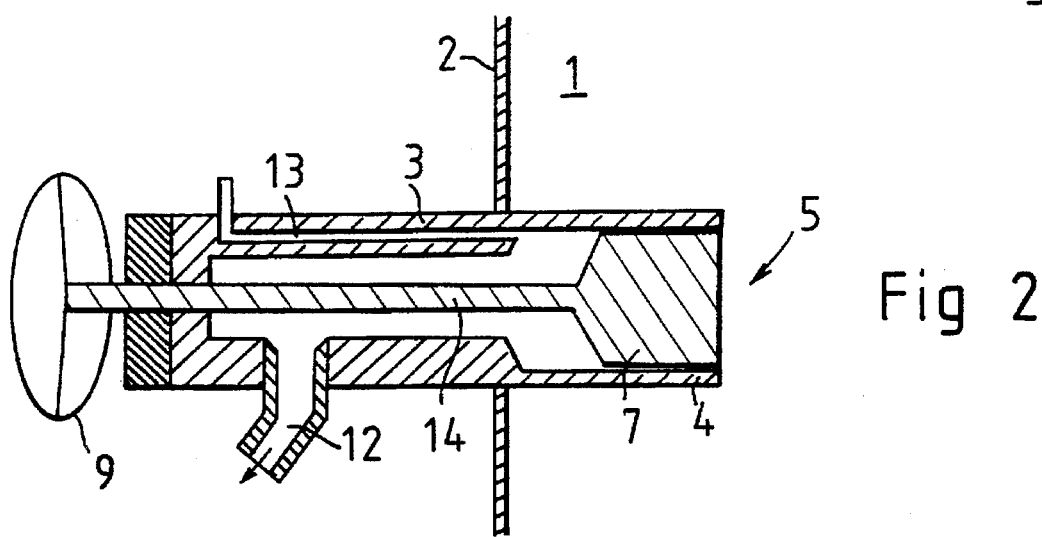
Figure 3:
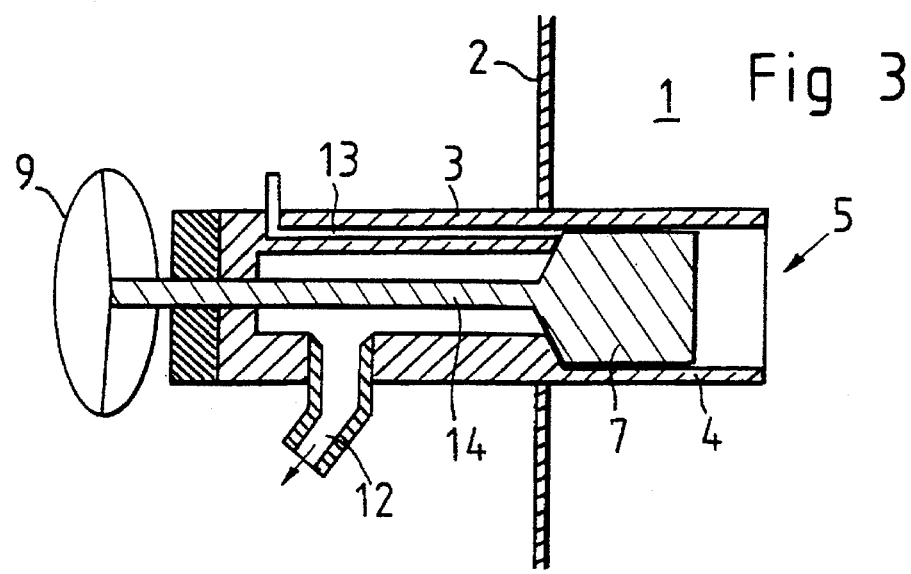

In the following, the invention is described in detail by the aid of an example by referring to the attached drawing, in which FIG. 1 presents a diagrammatic side view of the device of the invention according to one of its embodiments, with the piston in its intermediate position, mounted in a process pipe, FIG. 2 presents the device of FIG. 1 with the reciprocating valve in its front position, and FIG. 3 presents the device of FIG. 1 with the reciprocating valve in its rear position.

The figure shows a sectional side view of a device for taking a filtrate sample from slush pulp containing fibres. The device comprises a cylinder 3 limited by walls 4. The cylinder forms a cylinder space 6, and the cylinder is mounted on a wall of a process container 1 so that it goes through the wall, with its open end 5 towards the container 1. Mounted in the cylinder space 6 is a reciprocating valve 7 which can be moved backwards and forwards (reciprocates). The dimensions of the reciprocating valve 7 and cylinder 3 are so chosen that the gap between them forms a liquid canal 8 from the open cylinder end into the cylinder space behind the piston. The gap is of a size that blocks the entry of fibres from the slush pulp and only admits a filtrate through the gap. Moreover, the device comprises an actuator 9 for moving the reciprocating valve between the rear, intermediate and front positions. In the intermediate position, i.e. in FIG. 1, the reciprocating valve end has sunk through some distance into the open cylinder end, forming a special pocket limited by the cylinder walls 4 and the reciprocating valve end. This pocket opens freely into the container 1. In the front position, i.e. in FIG. 2, the piston end has been pushed substantially to the level of the open cylinder end to discharge the fibre accumulation into the container. Moreover, the cylinder is provided with a drain duct 12 to drain off the filtrate sample penetrating through the sampling duct into the space behind the reciprocating valve, the sample being passed e.g. into an analyzer or receiver for analysis.

The purpose of the pocket 10 is to gather slush pulp in it so that the slush pulp forms a kind of filter which only passes a filtrate of the slush pulp through it into the sampling duct 8 and further into the drain duct 12 while the fibre material remains in the pillow-like filter formed by the fibrous slush in the pocket.

When desired, the reciprocating valve can be pushed into the front position, causing the fibre material gathered in the pocket to be discharged into the container 1 and the device to be cleaned. At the same time, as the reciprocating valve moves in the cylinder space e.g. backwards and forwards as actuated by the actuator 9, the sampling duct 8 is also cleaned, so the device does not necessarily require separate and specific flushing and cleaning operations. At the same time, it is possible to introduce special flushing agent into the cylinder space behind the reciprocating valve through the flushing duct 13 to remove any fibre material or filtrate that may remain in the cylinder or sampling duct into the container 1.

In the embodiment described, the cylinder 3 and piston 7 have a gap between them that forms a sampling duct 8. Further, in the embodiment described, the cylinder is provided with a special flushing duct 13 for supplying wash water into the sampling duct 8 and/or into the drain duct 12 and for washing the sampling duct and/or drain duct with flush water flowing into the container 1. The piston is so designed that it closes the drain duct when in the rear position, i.e. in the position shown in FIG. 3. In this situation, the reciprocating valve closes the cylinder space 15 around the reciprocating valve rod 14, which forms the drain duct 12. The walls of the cylinder space 15 form a seat surface 16, against which the back surface of the reciprocating valve is pressed when the reciprocating valve is in its rear position, closing the drain duct tightly, i.e. no liltrate can penetrate into the drain duct while the reciprocating valve is in its rear position.

This application example is intended to illustrate the invention without limiting it in any way.

We claim:

1. A device for taking a liltrate sample from slush pulp containing fibers through a wall (2) of a container (1) containing pulp, said device comprising:

a cylinder (3) limited by walls (4) and forming a cylinder space (6) open at one end (5), said cylinder being mounted on the wall (2) so that it goes through the wall, with its open end (5) in the direction of the container (1);

a reciprocating valve element having an end that can move backward and forward within the cylinder and which is placed in the cylinder space;

a sampling duct (8) for passing a sample from the open cylinder space into the cylinder space behind the reciprocating valve element;

an actuator (9) for moving the reciprocating valve element;

a drain duct (12) for draining off the sample penetrating through the sampling duct into the space behind the reciprocating valve element for analysis;

characterized in that the reciprocating valve element has a rear position, in which it closes the drain duct (12), an intermediate position, in which the reciprocating valve element end has sunk through some distance into the open end (5) of the cylinder (3), forming a pocket (10) limited by the cylinder walls (4) and the reciprocating valve element end for gathering fibrous slush pulp and forming a pillow-like filter (11) in the pocket, and a front position, in which the reciprocating valve element end has been pushed at least mainly to the level of the open end of the cylinder for removing the pillow-like filter and emptying the pocket into the container.

2. Device as defined in claim 1, characterized in that the cylinder and reciprocating valve element form between them a gap that forms the sampling duct (8).

3. Device as defined in claim 2, characterized in that the gap consists of the clearance between the cylinder and the reciprocating valve element.

4. Device as defined claim 1, wherein the cylinder (3) is provided with a flushing duct (13) for supplying wash water into the sampling duct (8) and washing the sampling duct with wash water flowing into the container (1).

5. Device as defined in claim 1 wherein the cylinder (3) is provided with a flushing duct (13) and the reciprocating valve element (7) closes the flushing duct (13).

6. The device of claim 1 where the open end of the cylinder opens into the container.

7. The device of claim 1 where the open end of the cylinder opens inside the container.

8. The device of claim 1 further comprising a flushing duct for supplying wash water into the sampling duct and washing the drain duct with wash water flowing into the container.

9. The device of claim 1 further comprising a flushing duct for supplying wash water into the drain duct and washing the sampling duct with wash water flowing into the container.

10. The device of claim 1 further comprising a flushing duct for supplying wash water into the drain duct and washing the drain duct with wash water flowing into the container.

* * * * *